US008776721B1

(12) United States Patent
Allen

(10) Patent No.: US 8,776,721 B1
(45) Date of Patent: Jul. 15, 2014

(54) SYSTEM AND METHOD FOR HARVESTING EGGS FROM ARTHROPODS

(75) Inventor: Margaret L. Allen, Cleveland, MS (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 138 days.

(21) Appl. No.: 13/485,042

(22) Filed: May 31, 2012

(51) Int. Cl.
*A01K 29/00* (2006.01)
(52) U.S. Cl.
USPC .................................................. 119/6.6
(58) Field of Classification Search
USPC .................................... 119/6.5, 6.6
See application file for complete search history.

(56) References Cited

U.S. PATENT DOCUMENTS

| | | | | |
|---|---|---|---|---|
| 2,539,633 | A | * | 1/1951 | Morrill ........................... 119/6.5 |
| 2,970,565 | A | * | 2/1961 | Reynolds ........................ 119/6.5 |
| 5,113,799 | A | * | 5/1992 | Carr et al. ...................... 119/6.5 |
| 7,861,672 | B2 | * | 1/2011 | Power ............................ 119/236 |

* cited by examiner

*Primary Examiner* — Monica Williams
(74) *Attorney, Agent, or Firm* — John Fado; Robert D. Jones; Lesley Shaw

(57) ABSTRACT

The system and method for harvesting eggs from arthropods includes a modular arthropod egg repository that is essentially a plurality of substrates connected along a common edge in a tablet-type configuration. The egg repository is deployed in an arthropod containment vessel. Arthropods ambulate onto a repository substrate and implant eggs. Operators can selectively remove entire repositories or individual substrates (as required) from the containment vessel. The system allows operators to utilize batch, continuous, and semi-continuous culture methods to rear target arthropods.

16 Claims, 4 Drawing Sheets ly visible and accessible to other arthropods within the enclosure. Consequently the eggs are frequently cannibalized by the other arthropods. The eggs are also cannibalized by the arthropod larvae as they emerge from nearby hatched eggs.

SYSTEM AND METHOD FOR HARVESTING EGGS FROM ARTHROPODS

FIELD OF THE INVENTION

The present invention relates to a method and apparatus for collecting arthropod eggs for commercial production of arthropods. Specifically, the invention relates to a method and apparatus for collecting beetle eggs (e.g. *Colemegilla maculata*) for commercial production of arthropods that can be applied widely in the care and culture of terrestrial organisms that are important in agriculture, horticulture, the terrarium and pet hobby, environmental screening and toxicity testing, science instruction and education, gardening, and the education-entertainment fields.

BACKGROUND OF THE INVENTION

The pink-spotted lady beetle, *Coleomegilla maculata* De Geer (Coleoptera: Coccinellidae), is a generalist predator native to North America. In nature, it feeds on a wide range of soft-bodied insects and mites in managed and unmanaged landscapes. This quality makes *C. maculata* a desirable natural alternative to conventional pesticides and other chemical insect pest control means, particularly in a greenhouse setting. In its native range, *C. maculata* does not overwinter in houses or become a nuisance pest. *C. maculata* is amenable to rearing in artificial (i.e. non-natural) environments, which makes it a good prospect for commercial production. However, systems for rearing *C. maculata* on a large scale are virtually unknown.

One obstacle to commercial production of *C. maculata* and other similar arthropods is the lack of an efficient means to harvest the arthropod eggs. In nature, females prefer to oviposit on plants with epidermal hairs (trichomes). In laboratory conditions, individual females frequently oviposit on smooth surfaces such as containers of food or water or on the smooth surface of a petri dish. Removal of these eggs from the smooth surfaces is possible, but time consuming and often results in damaged eggs. Additionally, in a commercial-sized arthropod enclosure, multiple eggs are laid in open areas that are easily visible and accessible to other arthropods within the enclosure. Consequently the eggs are frequently cannibalized by the other arthropods. The eggs are also cannibalized by the arthropod larvae as they emerge from nearby hatched eggs.

The need exists for an arthropod egg containment apparatus and system that minimizes arthropod cannibalism and enables operators to quickly and efficiently harvest (i.e. remove) large volumes of arthropod eggs. The system and method described herein comprises a compact, modular device and associated system for safely, simply, inexpensively, and efficiently, containing and culturing terrestrial arthropod eggs. Batch, continuous, and semi-continuous culture methods are supported by the devices described herein.

SUMMARY OF THE INVENTION

This disclosure is directed to an arthropod egg repository. The repository comprises a plurality of substrates connected by a single connecting means. The substrates are positioned so that arthropods ambulate onto the substrate and deposit eggs. The substrates are structured so that an operator can manually remove individual substrates from the connecting means and thereby remove implanted eggs from the repository.

This disclosure is also directed to an arthropod rearing system. The rearing system includes a closed arthropod containment vessel. An arthropod egg repository is disposed within the vessel. The egg repository comprises at least three substrates connected together along one common edge. The substrates are structured to enable an arthropod to ambulate onto a substrate and implant an egg on the substrate. The substrate configuration enables an operator to remove a single substrate with an implanted egg, and then re-deploy the remaining substrates in the containment vessel.

This disclosure is further directed to a method of rearing arthropods. A plurality of substrates are connected together along a common edge to form a tablet-type configuration. The connected substrates comprise an egg repository. The egg repository is placed in a containment vessel so that arthropods ambulate onto the substrates and implant eggs.

DETAILED DESCRIPTION OF PREFERRED EMBODIMENTS

Figure 1:
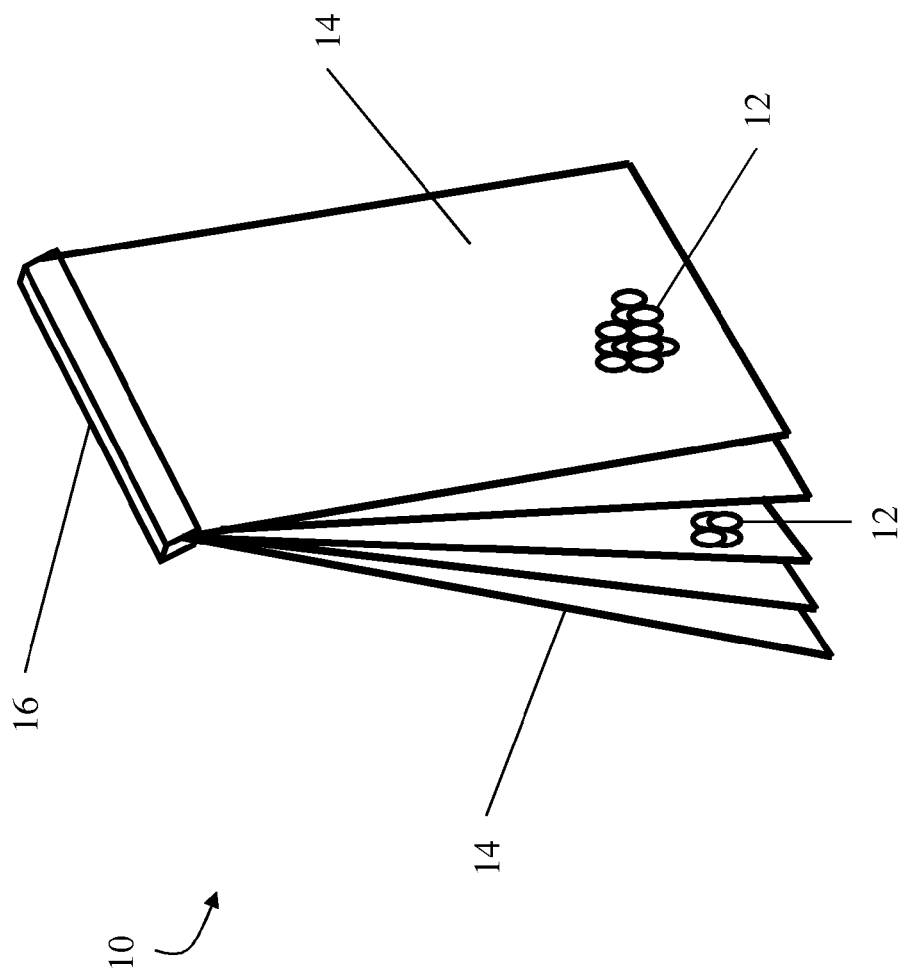
FIG. 1 is a perspective view of the hanging refugia.

As generally shown in FIG. 1, an important element of the system described herein comprises a "hanging refugia" 10. For the purposes of this disclosure, the refugia 10 is an arthropod egg repository comprising a plurality of substrates 14 configured in a tablet-like arrangement that enables target arthropods to ambulate between the substrates 14 and deposit eggs 12 on the surface of the substrates 14. The substrates 14 are generally secured along at least one edge by a separate and distinct connection means 16. For the purposes of this disclosure, the separate and distinct "connection means" 16 preferably comprises a chemical connection means (such as an adhesive) or a mechanical means (such as a clamp or pin), but may also include a magnetic connection means or any other separate and distinct connection means known in the art.

In the preferred embodiment, the substrates 14 are generally rectangular, however they may be any shape known in the art. The substrates 14 may be treated and/or saturated with various substances designed to attract egg-bearing females and to encourage the successful development of the eggs 12. These substances include various chemical attractants (such as food-based attractants) as well as actual nutrients for supporting the hatching larva. The substrates 14 may also be configured to mimic (to the extent possible) the textured surface of leaves found in the natural environment.

The substrates 14 may be comprised of a treated (or untreated) paper or polymer material. Alternatively, the substrates may be comprised of any substance known in the art. Further, the hanging refugia 10 may be designed to be selectively removed from an arthropod containment vessel 22 as a single unit, or as single individual substrates 14. The removal of individual substrates 14 allows an operator to sample or target only selected substrates where eggs 12 are implanted.

Figure 2:
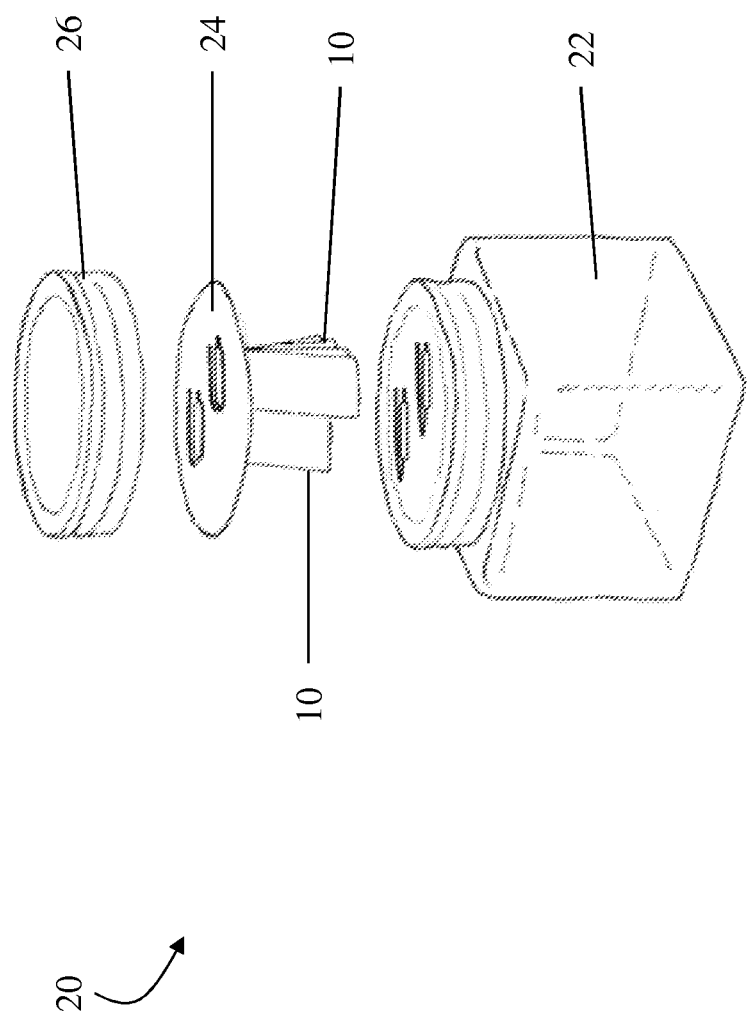
FIG. 2 is an assembly view of the arthropod containment system including the hanging refugia.
Figure 3:
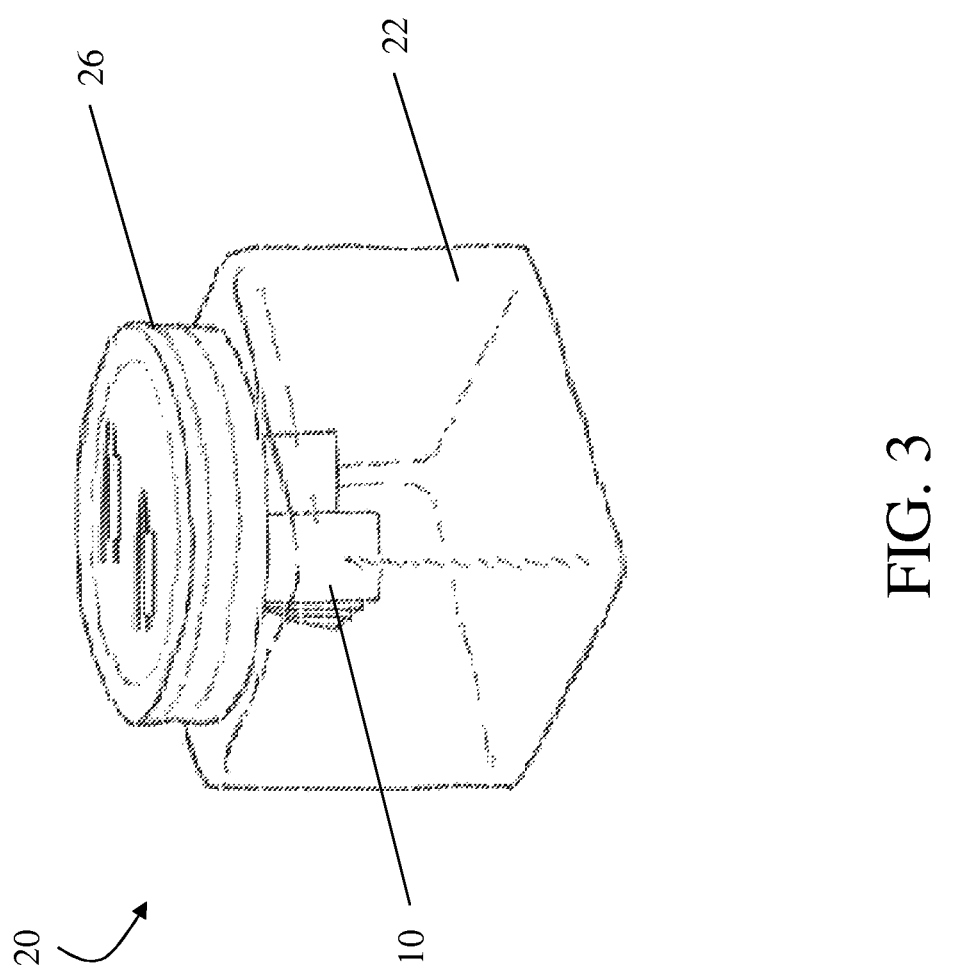
FIG. 3 is a perspective view of the arthropod containment system disclosed in FIG. 2.

FIG. 2 shows an assembly drawing of one embodiment of an arthropod rearing system 20 that incorporates the hanging refugia 10 shown in FIG. 1. FIG. 3 shows the system 20 in an assembled configuration. The system 20 comprises a relatively large, closed containment vessel 22. A removable egg and larvae collection module 24 (not clearly visible in FIG. 3) is secured to the containment vessel 22 by a lid-type connection device 24. Although FIGS. 2 and 3 show two refugia apparatuses 10, one or more than two of the apparatuses 10 may be attached to a single collection module 24.

Although the containment vessel 22 is shown as a cube-shaped jar, other shapes and configurations should be considered within the scope of this disclosure, consistent with the function of containing the target arthropods. Similarly, although a screw-type jar lid is shown, other types of collection module 24 connection devices 26 are also contemplated and should be considered to be disclosed herein.

Figure 4:
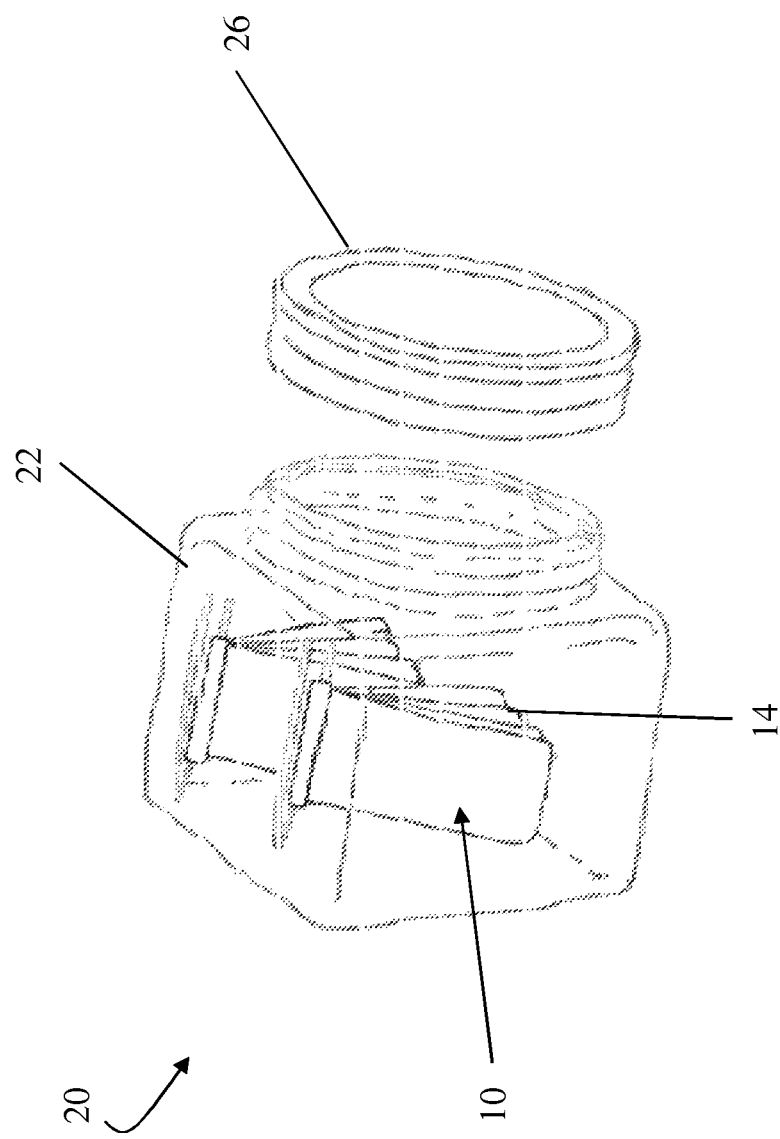
FIG. 4 is a perspective view of an alternative embodiment of the arthropod containment system.

FIG. 4 shows an alternative configuration of the system 22. The embodiment disclosed in FIG. 4 shows the containment vessel as horizontally oriented. This configuration may facilitate sampling and removal of individual substrates 14 and may also have other advantages. Specifically, the FIG. 4 embodiment allows an operator to remove individual substrates 14 without removing the entire hanging refugia from the containment vessel 22.

In a further alternative embodiment, the device shown in FIG. 4 may be deployed in a greenhouse or an outdoor environment without a lid/connection device 26 so that the containment vessel 22 is "open" and the refugia 10 is exposed to the outside environment. In this "open embodiment" of the system 20, the substrates 14 may be treated with an attractant so that arthropods from outside the containment vessel 22 are drawn into the containment vessel 22 and implant eggs 12 on the hanging refugia 10 in the vessel 22. This open embodiment enables an operator to effectively trap and/or sample (essentially) wild arthropods in a targeted area.

Although FIG. 4 shows a vessel 22 with a single entry/exit port, in the open embodiment, the vessel 22 may be modified to include multiple openings so that the vessel 22 is more open to the outside environment. In further open embodiments, the vessel 22 may be even further modified so that the "vessel" 22 essentially only comprises a support means for the refugia 10 so that the refugia 10 receives maximum exposure to the environment in a targeted area.

In operation, in the preferred embodiment, lady beetles or other arthropods are deposited into a containment vessel 22 of the type shown in FIGS. 2-4. The arthropods ambulate onto the hanging refugia substrates 14 and deposit their eggs 12 (best shown in FIG. 1) which eventually mature into larvae. Operators selectively open the containment vessel 22 and harvest individual substrates 14, individual refugia 10 containing multiple substrates 14, or the operator may harvest a collection module(s) 24 containing one or more refugia 10 (as best shown in FIG. 2).

The refugia 10 and system 20 described herein provide important advantages over the prior art. The refugia 10 substrates 14 are specifically treated and designed to attract females to oviposit on the substrates 14. The substrates 14 are also designed to facilitate the healthy development of arthropod larvae. The ability to remove the refugia 10 (and individual substrates 14) prevents the necessity to scrape the arthropod eggs off of containment housing surfaces (per the prior art). The method and apparatus described herein discourages cannibalization, and is faster, more efficient, and does not damage arthropod eggs as was common using prior art methods.

For the foregoing reasons, it is clear that the system described herein provides an innovative means of rearing arthropods and facilitating the harvest of arthropod eggs. The invention may be modified in multiple ways and applied in various technological applications. The current invention may be modified and customized as required by a specific operation or application, and the individual components may be modified and defined, as required, to achieve the desired result. Although lady beetles (specifically *Colemegilla maculata*) are generally discussed, the system may also be applicable to insects in the order coleoptera, hemiptera, diptera, embioptera, lepidoptera, hymenoptera, neuroptera, or any of the other minor orders of hexapoda, or a non-insect arthropod such as spiders, mites, scorpions, millipedes or others.

Although some of the materials of construction are not described, they may include a variety of compositions consistent with the function of the invention. Such variations are not to be regarded as a departure from the spirit and scope of the invention, and all such modifications as would be obvious to one skilled in the art are intended to be included within the scope of the following claims.

What is claimed is:

1. An arthropod rearing system comprising an arthropod containment vessel, including an arthropod egg repository comprising a plurality of substrates that are connected by binding the substrates together in a tablet-type formation so that each substrate abuts an adjacent substrate, the substrates being suspended within the vessel so that arthropods implant eggs on the substrates, the substrates being structured so that an operator can manually remove individual substrates and thereby remove implanted eggs from the repository;

wherein at least one surface of the substrates has a non-smooth surface, or at least one surface of the substrates is coated with an arthropod attractant or nutritional substance.

2. The arthropod rearing system of claim 1 wherein the plurality of substrates comprises three or more substrates.

3. The arthropod rearing system of claim 1 wherein each of the substrates comprises one of paper or a polymer.

4. The arthropod rearing system of claim 1 wherein at least one surface of the substrates is textured to resemble a plant.

5. The arthropod rearing system of claim 1 wherein the repository is structured so that the substrates hang vertically from a connecting means.

6. The arthropod rearing system of claim 1 wherein more than one repository is disposed within a closed containment vessel.

7. The arthropod rearing system of claim 1 wherein the vessel includes an opening on a lateral side of the vessel that enables an operator to selectively remove individual substrates from the vessel without removing the egg repository from the vessel.

8. The arthropod rearing system of claim 1 wherein the repository is structured so that each of the substrates is removable from the repository individually and without tools and without removing the egg repository from containment vessel.

9. The arthropod rearing system of claim 1 wherein a plurality of repositories are connected by a single collection module, the collection module being structured so that an operator can remove the plurality of repositories by removing the single collection module.

10. An arthropod rearing system comprising:
a closed arthropod containment vessel;
an arthropod egg repository suspended within the vessel, the repository comprising at least three substrates, the egg repository having a tablet-type formation;
whereby the substrates are structured to enable an arthropod to ambulate onto a substrate and implant an egg on the substrate, the substrates are further structured to enable an operator to remove a single substrate with an implanted egg, and then re-deploy the remaining substrates in the containment vessel, the substrates being bound together so that each substrate abuts an adjacent substrate.

11. A method of rearing arthropods comprising the steps of:
  (a) providing a plurality of substrates;
  (b) connecting the substrates together along a common edge to form a tablet-type configuration so that each substrate abuts an adjacent substrate, the connected substrates comprising an egg repository; and
  (c) placing the egg repository in a containment vessel wherein arthropods ambulate onto the substrates and implant eggs.

12. The method of claim 11 further comprising:
  (d) removing the egg repository from the containment vessel;
  (e) removing substrates that have implanted eggs; and
  (f) re-installing the egg repository with any remaining substrates back into the containment vessel.

13. The method of claim 11 further comprising:
  (d) opening the containment vessel;
  (e) removing any substrates with implanted eggs; and
  (f) closing the containment vessel.

14. The method of claim 11 wherein, in step (c), placing the egg repository in the containment vessel so that the substrates hang vertically downwardly.

15. The method of claim 11 wherein, in step (a) the substrates comprise three or more substrates treated with an arthropod attractant and/or arthropod nutritional substances.

16. The method of claim 11 wherein, in step (a), each of the substrates comprises one of paper or a polymer.

\* \* \* \* \*